United States Patent [19]
Kropf et al.

[11] Patent Number: 5,702,480
[45] Date of Patent: Dec. 30, 1997

[54] MODULAR HIP JOINT PROSTHESIS

[76] Inventors: Philipp Rolf Kropf, Haldenstrasse 25, 8142 Uitikon; Albert Geisser, Stationsstrasse 33, CH-6373, Ennetbürgen, both of Switzerland

[21] Appl. No.: 430,126

[22] Filed: Apr. 25, 1995

Related U.S. Application Data

[63] Continuation of Ser. No. 121,727, Sep. 15, 1993, abandoned.

[30] Foreign Application Priority Data

Oct. 13, 1992 [CH] Switzerland .................. 03193/92

[51] Int. Cl.$^6$ ............................................. A61F 2/36
[52] U.S. Cl. ............................................. 623/23
[58] Field of Search ............................. 623/23, 22

[56] References Cited

U.S. PATENT DOCUMENTS

| 4,516,277 | 5/1985 | Butel | 623/23 |
|---|---|---|---|
| 4,878,917 | 11/1989 | Kranz et al. | 623/18 |
| 4,892,550 | 1/1990 | Huebsch | 623/22 |
| 4,908,032 | 3/1990 | Keller | 623/18 |
| 4,938,773 | 7/1990 | Strand | 623/23 |
| 5,002,578 | 3/1991 | Luman | 623/23 |
| 5,080,685 | 1/1992 | Bolesky | 623/23 |
| 5,108,452 | 4/1992 | Fallin | 623/23 |
| 5,152,795 | 10/1992 | Sioshansi et al. | 623/16 |
| 5,314,479 | 5/1994 | Rockwood et al. | 623/19 |

FOREIGN PATENT DOCUMENTS

| 0243298 | 4/1987 | European Pat. Off. . | |
| 0399920 | 11/1990 | European Pat. Off. | 623/23 |
| 2580171 | 10/1986 | France | 623/23 |
| 2656519 | 7/1991 | France | 623/23 |
| 3340767 | 5/1985 | Germany | 623/22 |
| 4031520 | 4/1992 | Germany | 623/18 |
| 1739988 | 6/1992 | U.S.S.R. . | |
| 8911837 | 12/1989 | WIPO | 623/22 |
| 9301769 | 2/1993 | WIPO | 623/22 |

*Primary Examiner*—David H. Willse
*Attorney, Agent, or Firm*—The Firm of Gordon W. Hueschen

[57] ABSTRACT

The modular hip prosthesis has an axial stem forming its distal part. Two modular proximal parts can be mounted on the stem from its proximal end and be rigidly connected thereto.

Because the prosthesis has two modular parts at its proximal end, it can be optimally adapted to match the bone geometry intraoperatively. The diameter of the prosthesis in its proximal part and the position of the hip joint can be defined independently. Due to its slim shape and a drain for medullary material, the stem can directly be driven into the bone and does not require a pre-drilled cavity.

15 Claims, 2 Drawing Sheets

MODULAR HIP JOINT PROSTHESIS

The present application is a file wrapper continuation of prior-filed application Ser. No. 08/121,727, filed Sep. 15, 1993, now abandoned.

BACKGROUND OF THE INVENTION

1. Field of the Invention

The invention relates to a modular hip joint prosthesis for being driven into the femur.

2. Description of the Prior Art

Prostheses for replacing the joint of the hip and the femoral head are provided in various sizes and shapes, such that a fitting prosthesis can be found for any shape and state of degradation of a femur. The surgeon e.g. desires to have a free choice of the length and curving of the distal part and the diameter and shape of the proximal part of the prosthesis. It should also be possible to select the surface of the prosthesis depending on the use of bone cement in the proximal and/or distal regions of the bone.

For providing a variable prosthesis, several modular systems have been designed such as described in CH 671 689 and WO 88/01854. These systems consist usually of a module for the proximal section and one or two modules for the intermediary and distal section prosthesis, which can be combined to assemble the desired prosthesis.

Especially the proximal part can be variously shaped. Even if a modular system is used, it is therefore necessary that the surgeon disposes of a wide choice of different prostheses or proximal modules. This leads to high costs for acquiring and storing these parts.

Furthermore, existing modular systems must be assembled at least partially before being inserted into the bone and can hardly be modified intraoperatively in the bone (in situ).

Before driving conventional prosthesis into the femur, the bone must be reamed out for creating a cavity to receive the prosthesis. This is done by working the bone with suitable rasps or drills. Reaming out the femur leads often to problems because it weakens the bone structure. Furthermore, it is time consuming and demands a great skill of the surgeon because any reamed out material is lost. It also requires a set of reaming tools matched to the individual modular parts of the prosthesis.

To avoid reaming out the femur at least in its distal part, prostheses have been proposed that have a distal end consisting of a thin rod or one or more wires. These can directly be driven into the soft bone without preparing a cavity. Such prostheses are, however, poorly held in the femur since their distal ends are only supported by the soft bone. Furthermore, they do not provide enough pressure on the hard bone to stimulate a growth of the bone.

SUMMARY OF THE INVENTION

Therefore it is an object of the invention to provide a modular prosthesis that does not have all the disadvantages described above and can be fully assembled intraoperatively in the bone (in situ).

Now, in order to implement these and still further objects of the invention, which will become more readily apparent as the description proceeds, the inventive prosthesis is manifested by the features that it comprises a stem as its distal part and a plurality of modular proximal parts, wherein said modular proximal parts are attachable to said stem from a proximal end of said stem.

Such a prosthesis can be assembled during the operation and the individual modules can be added consecutively from the proximal end of the prosthesis. This simplifies the insertion of the prosthesis considerably and renders it easy to make corrections during the operation. Especially, it is possible to choose and try the modular parts intraoperatively.

Since the prosthesis consists of several modules in its proximal part, it is possible to define its most important parameters (the thickness of the metaphysary part and the angle of projection and distance of the head of the hip joint) separately by selecting suitable modules.

In its preferred embodiment the stem can be driven into the distal part of the bone without requiring any reaming or drilling of the femur. Still it provides good contact with the hard bone, which stimulates bone growth and provides an intimate connection between the stem and the bone.

The stem is especially suited for being driven into the bone by a oscillatory percussion tool such as it is e.g. described in the European patent application EP 452 543. In a preferred embodiment the proximal end of the stem is shaped to provide a rigid connection with the percussion tool to transfer pulling, pushing and rotating forces. This improves the control over the position of the stem while it is being driven into the femur.

The stem can be very long such that the prosthesis can be driven deeply into the bone. This is a big advantage during secondary installations where the removing of an older stem has lead to damages of the tubular bone in its upper or middle section. Such a long stem has an effect comparable to an intramedullary nail and strengthens the femur.

BRIEF DESCRIPTION OF THE DRAWINGS

The invention will be better understood and objects other than those set forth above will become apparent when consideration is given to the following detailed description thereof. Such description makes reference to the annexed drawings, wherein.

DESCRIPTION OF THE PREFERRED EMBODIMENT

Figure 1:
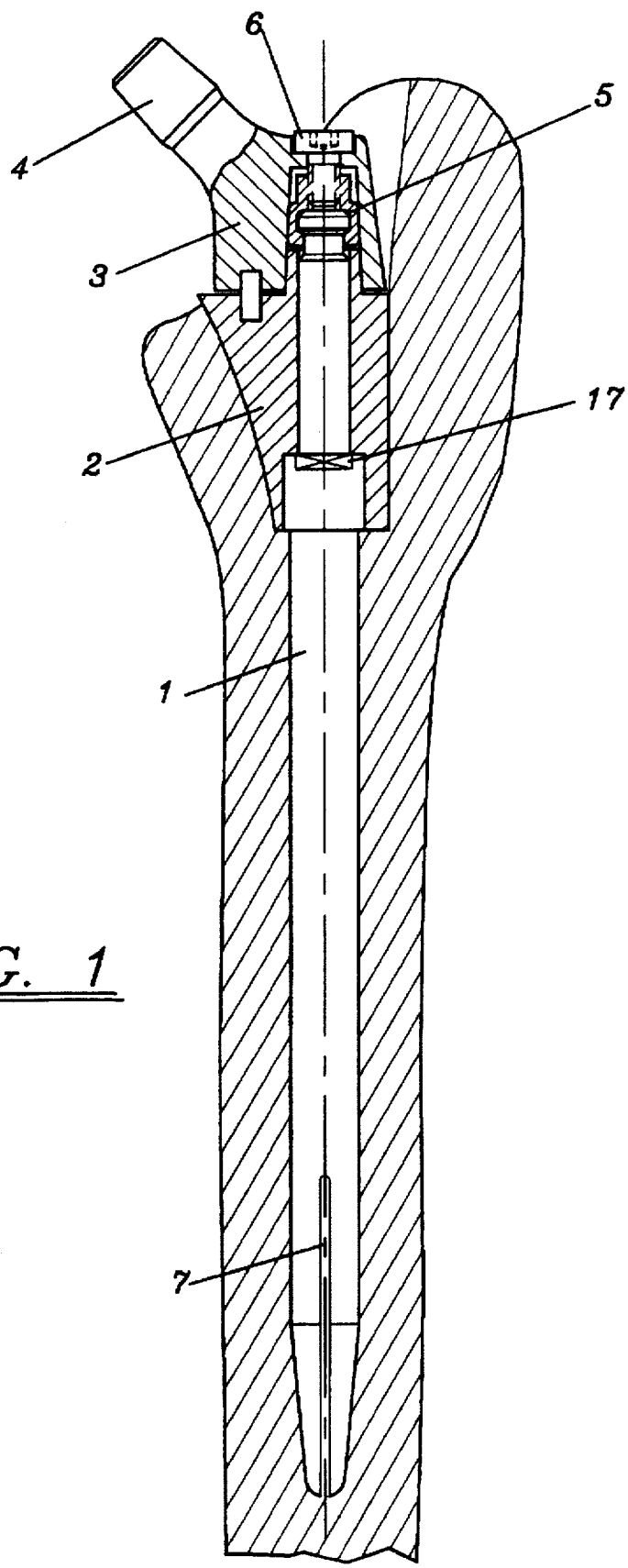
FIG. 1 is a sectional view of the prosthesis.

FIG. 1 shows a preferred embodiment of the inventive prosthesis. It substantially consists of three parts: the stem 1, the metaphysary part 2 and the cervical part 3.

The stem 1 extends over nearly the whole length of the prosthesis, its lower end forming its distal part.

The metaphysary part 2 is slipped onto the stem 1 from its proximal end. This part defines the shape and diameter of the prosthesis in the proximal part of the femur.

The cervical part 3 is mounted on the metaphysary part 2 and connected to the stem 1 via a coupling 5 and a screw 6. This connection pulls the cervical part 3 towards the stem 1. For receiving the ball of the hip joint (not shown), the cervical part comprises a conventional, laterally projecting neck and cone 4. The length of this neck as well as its position and angle of projection defines the position of the ball of the hip joint.

Figure 2:
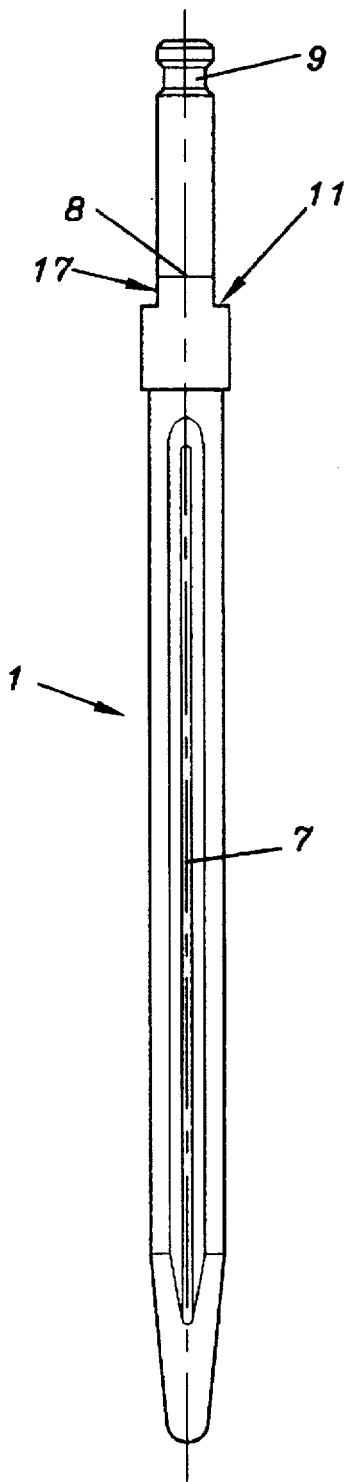
FIG. 2 shows the stem of the prosthesis.
Figure 3:
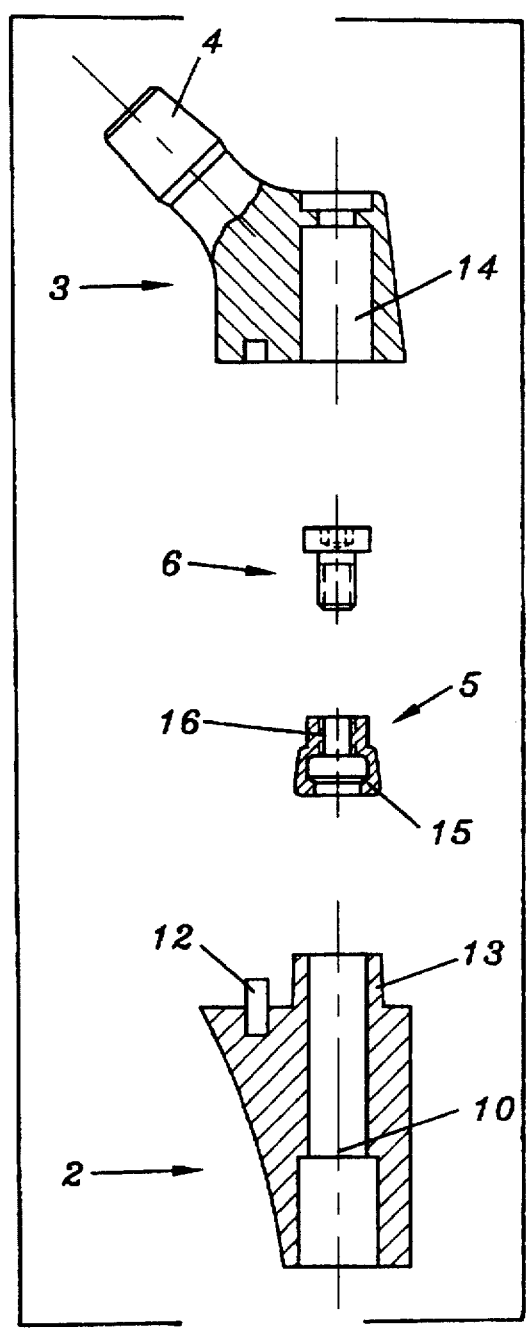
FIG. 3 shows the metaphysary and cervical parts as well as their connecting elements.

FIGS. 2 and 3 show the individual parts of the preferred embodiment of the inventive prosthesis in detail.

The stem 1 shown in FIG. 2 is rotated by 90° in respect to the stem shown in FIG. 1. The stem can be divided into an upper, proximal head 8 and a distal section. The distal section is slightly tapered at its bottom end and has a slowly varying or constant diameter otherwise, which substantially corresponds to the inner diameter of the hard bone. Depending on the size of the femur and its state of degradation, this diameter can be between 7 and 23 mm. Furthermore, the stem 1 can be provided with a longitudinal notch 7. This notch forms a drain for the medullary material when the prosthesis is driven into the femur. This makes it possible to drive the stem directly into the unprepared tubular bone and obviates the need for preparing a cavity.

The proximal end of the stem 1 is adapted to form a rigid connection to a percussion tool. Therefore, it is provided with a circumferential groove 9 to be engaged by the tool. It also has flat lateral faces 17, which can abut on corresponding faces of the tool. In this way, the connection with the tool can transfer pulling, pushing and rotational forces. This allows an optimum control of the orientation of the stem while it is driven into the bone.

The metaphysary part 2 is shown in FIG. 3. As described above, it defines the shape of the prosthesis in the proximal part of the femur. For this purpose it has a diameter that gradually decreases with increasing distance from its proximal end.

An opening 10 extending through the metaphysary part is formed to receive the head 8 of the stem 1. The metaphysary part 2 can therefore be slipped over the stem from its proximal end and is resting on its shoulder 11.

The connection between the metaphysary part 2 and the stem 1 can either be pivotal or fixed. For a fixed connection, the shoulder 11 and the opening 10 can be provided with notches or interlocking profiles.

The cervical part 3 is resting on the metaphysary part 2. The length and angle of its neck and cone 4 define the position and distance of the hip joint.

For receiving the slightly frusto-conical neck 13 of the metaphysary part, the cervical part has a matching opening 14. A peg 12 secures the two parts against rotation.

A coupling member 5 and a screw 6 are used for connecting the cervical part 3 to the stem 1. The coupling part 5 is shaped to be slipped over the proximal part of the stem 1 and has spring arms 15 to engage the circumferential groove 9. In the assembled state of the prosthesis, the coupling member 5 is enclosed by the lower part of the opening 14 of the cervical part 3. This prevents the arms 15 from being disengaged.

A threading is formed in the upper part of the coupling member 5 to receive a screw 6.

In this way, the screw 6 and the coupling member 5 provide a rigid connection between the cervical part 3 and the stem 1 that clamps the metaphysary part 3 tightly onto the stem 1.

As described above, the stem 1 is preferably driven into the femur before parts 2 and 3 are attached to it. When using the described embodiment of the stem, it is not necessary to prepare a cavity in the bone before inserting the stem. Using the oscillatory percussion tool described previously, pressure peaks, which could lead to a damage of the bone, can be avoided. Medullary material is drained through the notch 7.

In a next step, the metaphysary part 2 is slipped onto the proximal end 8 of the stem. Before doing so, it might be necessary to ream out at least part of the proximal femur. However, reaming out can often be dispensed with if the oscillatory percussion tool described above is used for driving the metaphysary part 2 onto the stem. In this case the damage of proximal bone material is small and a good connection between prosthesis and bone is achieved. The resulting, homogeneous pressure in the bone stimulates its growth.

If the metaphysary part 2 is driven into the bone with an oscillatory percussion tool, a suitable adapter can be used for connecting the part 2 and the tool. For this purpose, a threading can be formed on the head 13 of the metaphysary part, which can be screwed into an adapter tube.

After the insertion of the stem 1 and the metaphysary part 2, the coupling member 5 and the cervical part 3 are slipped over the proximal end of the stem 1.

Finally, the screw 6 is screwed from the proximal end of the cervical part 3 into the coupling member 5. At this point, the prosthesis is fully assembled.

It is also possible to assemble the prosthesis before driving it into the bone. In this case it is advisable to use a suitable adapter for rigidly coupling the percussion tool to the prosthesis. This adapter can e.g. replace the screw 6 and have a threading at its bottom end to be screwed into the coupling 5. The upper end of the adapter can e.g. be formed like the head 8 of the stem 1.

It is also possible to drive an only partially assembled prosthesis into the bone, consisting e.g. of the stem 1, the metaphysary part 2 and the coupling member 5. In this case, the adapter can be slipped over the neck 13 of the metaphysary part, suitably secured against rotation, and screwed into the coupling member 5.

The preferred embodiment described above is, of course, not the only possibility to realize the inventive prosthesis. In the following, some advantageous variations shall be discussed briefly.

In FIGS. 1 to 3 the stem 1 was shown to be straight. It can also be bent to match the form of the femur in its distal part.

The drain 7 is not necessary if the prosthesis is to be driven into a drilled out or hollow tubular bone. It can also be advisable to use a stem without drain if bone cement is to be used in to distal section of the prosthesis.

The stem can also be hollow and provided with a plurality of holes. Such a stem can be filled by bone material. Furthermore, a hollow stem can have elastic properties that better match those of the bone.

It is also possible to use more than two modular parts 2, 3 in the proximal section of the prosthesis. The cervical part 2 can e.g. be split into an upper and a lower part, thereby increasing the number of variations that can be used to fit the shape and state of the femoral head.

When the bone is afflicted by a tumor or if a secondary prosthesis must be inserted in a damaged bone, it may be necessary to cut off the proximal part of the femur. This proximal part must be replaced by a suitable prosthesis, which must be anchored distally. In such a case it is useful to provide a metaphysary part with a cylindric shape or a bone shape.

The head 8 of the stem and the connections between the modular parts 2 and 3 can also be realized in various ways. It is e.g. possible to make the head 8 detachable after insertion of the stem into the bone by screwing it into the stem. The same threading in the stem can then be used for screwing the metaphysary and the cervical part to the stem by using a long screw, which screw can be replace the short screw 6 and the coupling element 5.

In a further embodiment of the invention, the head 8 of the stem 1 and the neck 13 of the metaphysary part 2 are slightly conical. The connection can then be established by jamming the modular parts 1 to 3 into each other and securing the assembly by a screw.

While there are shown and described present preferred embodiments of the invention, it is to be distinctly understood that the invention is not limited thereto, but may be otherwise variously embodied and practiced within the scope of the following claims.

We claim:

1. A modular hip joint prosthesis comprising a stem forming a distal part of said prosthesis,
   a metaphysary part attachable to said stem from a proximal end of said stem and having a diameter increasing towards a proximal end of said metaphysary part, an outer surface of said metaphysary part providing a widening surface section of said prosthesis, and
   a cervical part attachable to said stem from said proximal end of said stem and carrying a laterally-projecting neck for receiving a ball or head of the hip joint, said cervical part alone defining the angle of projection of said laterally-projecting neck,
   wherein said proximal end of said stem extends into said cervical part and comprises a circular circumferential groove and flat lateral faces facing outwardly for rigidly connecting said stem to a tool for driving said stem into a bone,
   wherein said distal part is threadless and extends from said metaphysary part,
   and wherein said stem, said metaphysary part, and said cervical part are three separate modular parts.

2. The prosthesis of claim 1, wherein said cervical part is rigidly connected to said proximal end of said metaphysary part so that said cervical part is not rotatable in respect to said metaphysary part.

3. The prosthesis of claim 1, wherein said cervical part is adjacent to said proximal end of said metaphysary part.

4. The prosthesis of claim 3, comprising means for pulling said cervical part against said stem, thereby pushing said metaphysary part toward said stem.

5. The prosthesis of claim 1, wherein a distal section of said stem has a diameter between 7 mm and 23 mm.

6. The prosthesis of claim 1, wherein said neck is an integral portion of said cervical part.

7. A modular hip joint prosthesis comprising a stem forming a distal part of said prosthesis,
   a metaphysary part attachable to said stem from a proximal end of said stem and having a diameter increasing towards a proximal end of said metaphysary part, an outer surface of said metaphysary part providing a widening surface section of said prosthesis,
   a cervical part adjacent to said proximal end of said metaphysary part, attachable to said stem from said proximal end of said stem, and carrying a laterally-projecting neck for receiving a ball or head of the hip joint, said cervical part defining the angle of projection of said laterally-projecting neck, and
   a coupling means engaging said cervical part and said stem for pulling said cervical part against said stem, thereby pushing said metaphysary part against said stem,
   wherein said coupling means comprises
      a coupling member with arms engaging a circular circumferential groove of a proximal end of said stem and
      a threading for receiving a screw,
      wherein said coupling means is located in an opening of said cervical part and wherein walls of said opening prevent said arms from disengaging said groove.

8. The prosthesis of claim 7, wherein said metaphysary part and a shoulder of said stem comprises interlocking profiles.

9. The prosthesis of claim 7, wherein said stem extends through said metaphysary part and into said cervical part.

10. A modular hip joint prosthesis comprising a stem forming a distal part of said prosthesis,
    a metaphysary part axially attachable to said stem from a proximal end of said stem and having a diameter increasing towards a proximal end of said metaphysary part, an outer surface of said metaphysary part providing a widening surface section of said prosthesis,
    a cervical part axially attachable to said stem from said proximal end of said stem and carrying a laterally-projecting neck for receiving a ball or head of the hip joint, said cervical part alone defining the angle of projection of said laterally-projecting neck, wherein said stem extends through said metaphysary part and into said cervical part,
    wherein said stem, said metaphysary part, and said cervical part are three separate modular parts.

11. The prosthesis of claim 10 further comprising means for pulling said stem toward a proximal end of said cervical part.

12. The prosthesis of claim 10, wherein said means for pulling said stem comprises a coupling member with spring arms engaging a circular circumferential groove of a proximal end of said stem and with a threading for receiving a screw, wherein said coupling member is located in an opening of said cervical part and wherein walls of said opening prevent said spring arms from disengaging said groove.

13. The prosthesis of claim 11, wherein a distal end section of said metaphysary part abuts against a shoulder of said stem and a proximal end section of said metaphysary part abuts against said cervical part.

14. The prosthesis of claim 10, wherein said metaphysary part comprises a frusto-conical section reaching into a matching opening of said cervical part and wherein said stem extends through said frusto-conical section into said cervical part.

15. A modular hip joint prosthesis comprising a stem forming a distal part of said prosthesis,
    a metaphysary part attachable to said stem from a proximal end of said stem and having a diameter increasing towards a proximal end of said metaphysary part, an outer surface of said metaphysary part providing a widening surface section of said prosthesis,
    a cervical part attachable to said stem from said proximal end of said stem and carrying a laterally-projecting neck for receiving a ball or head of the hip joint, said cervical part alone defining the angle of projection of said laterally-projecting neck, and
    a coupling means for pulling said stem toward said cervical part, said coupling means comprising
       arms for engaging a circular circumferential groove of a proximal end of said stem and
       a threading for receiving a screw,
    wherein said coupling means is located in an opening of said cervical part and wherein walls of said opening prevent said arms from disengaging said groove.

* * * * *